(12) United States Patent
Al-Haimi et al.

(10) Patent No.: US 11,263,185 B2
(45) Date of Patent: Mar. 1, 2022

(54) METHODS AND SYSTEMS FOR AUTOMATING CLINICAL DATA MAPPING AND TRANSFORMATION

(71) Applicant: PerkinElmer Informatics, Inc., Waltham, MA (US)

(72) Inventors: Abdul Al-Haimi, Waterloo (CA); Chad Millen, Guelph (CA)

(73) Assignee: PerkinElmer Informatics, Inc., Waltham, MA (US)

( * ) Notice: Subject to any disclaimer, the term of this patent is extended or adjusted under 35 U.S.C. 154(b) by 408 days.

(21) Appl. No.: 16/356,187

(22) Filed: Mar. 18, 2019

(65) Prior Publication Data

US 2019/0286620 A1    Sep. 19, 2019

Related U.S. Application Data

(60) Provisional application No. 62/645,133, filed on Mar. 19, 2018.

(51) Int. Cl.
*G06F 17/00* (2019.01)
*G06F 7/00* (2006.01)
(Continued)

(52) U.S. Cl.
CPC ......... *G06F 16/211* (2019.01); *G06N 3/0454* (2013.01); *G06N 3/08* (2013.01); *G16H 10/20* (2018.01)

(58) Field of Classification Search
CPC .... G06F 16/211; G16H 10/20; G06N 3/0454; G06N 3/08
(Continued)

(56) References Cited

U.S. PATENT DOCUMENTS 8,244,702 B2 * 8/2012 Dettinger ............ G06F 16/2423
707/700
9,430,114 B1 * 8/2016 Dingman ................ G06F 3/048
(Continued)

OTHER PUBLICATIONS

Z. Li, X. Zhang, G. A. Mohua, and Vassili Karanassios, Artificial Neural Networks (ANNs) for Spectral Interference Correction Using a Large-Size Spectrometer and ANN-Based Deep Learning for a Miniature One, https://www.intechopen.com/books/advanced-applications-for-artificial-neural-networks/artificial-neural-networks-anns-for-spectral-interference-correction-using-a-large-size-spectrometer, Dec. 20, 2017, Downloaded Jul. 17, 2019, 24 pages.
(Continued)

*Primary Examiner* — Pavan Mamillapalli
(74) *Attorney, Agent, or Firm* — Banner & Witcoff, Ltd.

(57) ABSTRACT

Aspects discussed herein relate to employing deep learning to automate mapping and transformation of a source data set to a target data schema. A system may utilize deep learning algorithms to determine a mapping from the source schema to the target schema through identifying the source schema and creating a correspondence between source fields and target fields, and a corresponding data transformation. Artificial neural networks, configured as schema-level and instance-level classifiers, may generate a set of predictions based on the fields of the source data set and fields of the target data schema. These predictions may be combined with other predictions based on other criteria (such as similarity between the fields) to generate a complete prediction of a schema mapping. Similarly, deep learning techniques may be employed to determine an appropriate data transformation to transform source data content to an appropriate format for corresponding fields of the target schema.

23 Claims, 5 Drawing Sheets

(51) Int. Cl.
  *G06F 16/21* (2019.01)
  *G16H 10/20* (2018.01)
  *G06N 3/04* (2006.01)
  *G06N 3/08* (2006.01)
(58) Field of Classification Search
  USPC .......................................................... 707/756
  See application file for complete search history.

(56) References Cited

U.S. PATENT DOCUMENTS

| | | | |
|---|---|---|---|
| 10,248,736 B1* | 4/2019 | Carroll | G06F 16/258 |
| 10,453,476 B1* | 10/2019 | Aryal | G06N 3/084 |
| 10,649,965 B2* | 5/2020 | Barbas | G06F 16/214 |
| 10,726,036 B2* | 7/2020 | Schikora | G06F 16/211 |
| 10,810,654 B1* | 10/2020 | Robertson | G06F 16/258 |
| 2004/0078240 A1* | 4/2004 | Katz | G16H 10/60 |
| | | | 705/3 |
| 2004/0158567 A1* | 8/2004 | Dettinger | G06F 16/211 |
| | | | 707/E17.006 |
| 2005/0278139 A1 | 12/2005 | Glaenzer et al. | |
| 2008/0059241 A1* | 3/2008 | Zahlmann | G16H 10/20 |
| | | | 705/3 |
| 2009/0138167 A1* | 5/2009 | Gepperth | G06K 9/00805 |
| | | | 701/70 |
| 2013/0332194 A1 | 12/2013 | D'Auria et al. | |
| 2014/0324857 A1* | 10/2014 | Hazelwood | G06F 16/86 |
| | | | 707/736 |
| 2015/0363688 A1* | 12/2015 | Gao | G06F 16/9032 |
| | | | 706/27 |
| 2017/0052970 A1* | 2/2017 | Crabtree | G06F 16/2379 |

OTHER PUBLICATIONS

Jun. 17, 2019—(WO) International Search Report and Written Opinion—App PCT/US2019/022759.

* cited by examiner

METHODS AND SYSTEMS FOR AUTOMATING CLINICAL DATA MAPPING AND TRANSFORMATION

CROSS-REFERENCE TO RELATED APPLICATION

This application claims priority as a non-provisional of U.S. Prov. Pat. App. No. 62/645,133, titled "Methods and Systems for Automating Clinical Data Mapping and Transformation" and filed Mar. 19, 2018. The entirety of the foregoing application is incorporated herein by reference.

FIELD

This disclosure relates generally to methods and systems for automating a process for mapping clinical data to standard data schemas to transform the clinical data into a unified form that can have the effect of correcting and controlling for poor data quality.

BACKGROUND

Clinical data often comes in many formats. The site where the data is generated can dictate the format. In other instances, the underlying protocols that govern the collection of the data or other similar data collection constraints can dictate the format of the collected data. The results of a clinical study therefore often result in data having disparate data formats.

Each company and organization seeking approval for the data resulting from a clinical study must conform that data to accepted standards. Pharmaceutical companies, research organizations and other similar institutions must spend a multitude of time and resources to manually map raw clinical data to various standard data schemas that are accepted by the FDA and other regulatory bodies, and then transform the raw clinical data to a unified form that accounts for and corrects any data quality issues that may result from the disparate data formats inherent in raw clinical data. It would be therefore advantageous to find a system or method to reduce the time and resources needed to prepare clinical study results for submission to a regulatory body by, for example, reducing an amount of human intervention required to map and transform clinical data. Such systems or methods would not only reduce the cost of preparing data for submission, it would also increase the consistency with which the raw clinical data is mapped and transformed.

SUMMARY

Described herein are systems and methods for mapping and transforming raw clinical data. Clinical data, such as data resulting from clinical tests carried out to demonstrate the efficacy and safety of a medical product, may be input into a clinical data analysis system that may synthesize the raw clinical data so that it can be analyzed and used to generate reports and alerts.

Aspects discussed herein may map the raw clinical data to a target schema using a schema mapping process that runs the raw data through multiple classification algorithms to generate probability matrices indicative of a predicted data schema and the probability that the predicted data schema is the correct schema. A weighted probability matrix may be generated using the probability matrices and a maximum matching algorithm may be used to choose the best schema based on the weighted probability matrix.

After mapping the raw clinical data to a schema, the raw data may be run through a transformation process which may compare the content and column names of the raw data to a library of known transformations. Using a prediction model, the system may predict the correct transformation to generate content corresponding to the source data but formatted according to the target data schema. In some instances the predicted transformation can be based upon the schema mapped to a set of raw clinical data.

Once raw clinical data has been mapped and transformed, it may be stored in a central data repository where it can be used by the schema mapping process and the transformation process to make future mapping and transformation predictions. The stored mapped and transformed data can also be used by other aspects of the clinical data analysis system. For example, single studies can be downloaded for further analysis or to perform cross study analyses using the clinical data analysis system.

Thus, some aspects may provide a computer implemented method for data mapping and transformation. The method may comprise determining a source data set for transformation to a unified target data schema. The source data set may include a source data records organized according to a source data schema. The source data schema may include a plurality of source fields. The computer may determine a target data platform, and the target data platform may be associated with a target data schema similarly including a plurality of target fields.

The computer may generate a schema mapping based on a schema-level classifier, an instance-level classifier, and one or more similarity measurements. The computer may pre-process one or more fields of the source data set to render the data more suitable to further processing. The computer may generate a schema-level prediction for a target mapping of a first source field, of the plurality of source fields, based on output of a schema-level classifier. The schema-level classifier may comprise a first artificial neural network trained based on first example mappings between source field names and target field names. The computer may also generate an instance-level prediction for the target mapping of the first source field based on output of an instance-level classifier. The instance-level classifier may comprise a second artificial neural network trained based on second example mappings between source field data record characteristics and target field data record characteristics. The computer may generate one or more similarity predictions for the target mapping of the first source field based on one or more similarity measurements. For example, the computer may generate predictions based on a longest common subsequence criteria and/or a Levenshtein distance criteria. The computer may generate a schema mapping that maps the source data schema to the target data schema based on a weighted combination of the schema-level prediction, the instance-level prediction, and the one or more similarity predictions for the target mapping of the first source field.

The computer may determine appropriate data transformations to apply to the source data to generate the target data in an appropriate form. As with determining the mapping, the computer may pre-process one or more fields of the source data set. Based on the schema mapping, the computer may determine a transformation operative to transform source data content to appropriately formatted target data content. The computer may generate, based on a first target field associated with a first source field in the schema mapping, a first data transformation for portions of each source data record corresponding to the first source field. The computer may generate the one or more predictions for the first data transformation based on output of a data classifier. The data classifier may comprise a third artificial neural network trained based on example transformations for data corresponding to the first source field and the associated first target field. The computer may, additionally and/or alternatively, determine the data transformation based on a rules-based data conversion known to the system for certain types of fields. The determined transformation may be applied to portions of each source data record corresponding to each field of the target schema to generate a target data set. The target data set may be stored by the computer and/or related systems. The target data set may be in a unified target data schema amenable to review by one or more analytic tools, despite the source data being in a format unsuitable for those tools.

Aspects herein may incorporate deep learning techniques to allow users to correct misclassified mappings and transformations. These corrected examples may be fed back into the deep learning training processes for the schema-level, instance-level, and transformation classifiers. This may allow the system to grow in accuracy and usefulness as additional examples become known to the system.

Aspects described herein may find particular use in combination with features described by one or more of the inventors in prior applications. For example, the deep learning techniques may be used to implement aspects of the clinical data caching features described in U.S. application Ser. No. 15/233,847, titled "Caching Technology for Clinical Data Sources" and filed Aug. 10, 2016, the entirety of which is incorporated herein by reference. As another example, the table merge user interface of U.S. application Ser. No. 15/247,821, titled "Systems and Method Employing Merge Technology for the Clinical Domain" and filed Aug. 25, 2016, the entirety of which is incorporated herein by reference, may be employed according to aspects herein to present the predicted schema mapping to the user for review and modification. As still another example, the pluggable data connectors in U.S. application Ser. No. 15/247,825, titled "Clinical Connector and Analytical Framework" and filed Aug. 25, 2016, the entirety of which is incorporated herein by reference, may be used to effect the import and transfer of data from the source data set to the target data set, and the pluggable connectors may be improved to implement the data transformations and/or schema mappings determined by the system.

Corresponding apparatus, systems, and computer-readable media are also within the scope of the disclosure.

These features, along with many others, are discussed in greater detail below.

BRIEF DESCRIPTION OF THE FIGURES

The present disclosure is illustrated by way of example and not limited in the accompanying figures in which like reference numerals indicate similar elements and in which.

DETAILED DESCRIPTION

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope of the present disclosure. Aspects of the disclosure are capable of other embodiments and of being practiced or being carried out in various ways. Also, it is to be understood that the phraseology and terminology used herein are for the purpose of description and should not be regarded as limiting. Rather, the phrases and terms used herein are to be given their broadest interpretation and meaning. The use of "including" and "comprising" and variations thereof is meant to encompass the items listed thereafter and equivalents thereof as well as additional items and equivalents thereof.

By way of introduction, aspects discussed herein may relate to methods and techniques employing deep learning to assist and/or automate mapping and transformation of a source data set to a target data schema. Source clinical data may exist in many formats, stored according to various source data schemas. But analytics tools may expect data to be in a specific target data schema. According to some aspects, a system may utilize deep learning algorithms to determine a mapping from the source schema to the target schema through identifying the source schema and creating a correspondence between source fields and target fields, and a corresponding data transformation. Artificial neural networks, configured as schema-level and instance-level classifiers, may generate a set of predictions based on the fields of the source data set and fields of the target data schema. These predictions may be combined with other predictions based on other criteria (such as similarity between the fields) to generate a complete prediction of a schema mapping between the source and target schemas. The predicted schema mapping may be presented to a user for review and correction. User changes may be fed back into the deep learning training process to provide improved accuracy in future processing. Similarly, deep learning techniques may be employed to determine an appropriate data transformation to transform source data content to an appropriate format for corresponding fields of the target schema. The transformed data may be stored on the target data platform and made available to computer analytics systems. This may allow various sets of source clinical trial data, each having disparate formats, to be converted into a unified format suitable for analysis in the computer analytics system.

Figure 1:
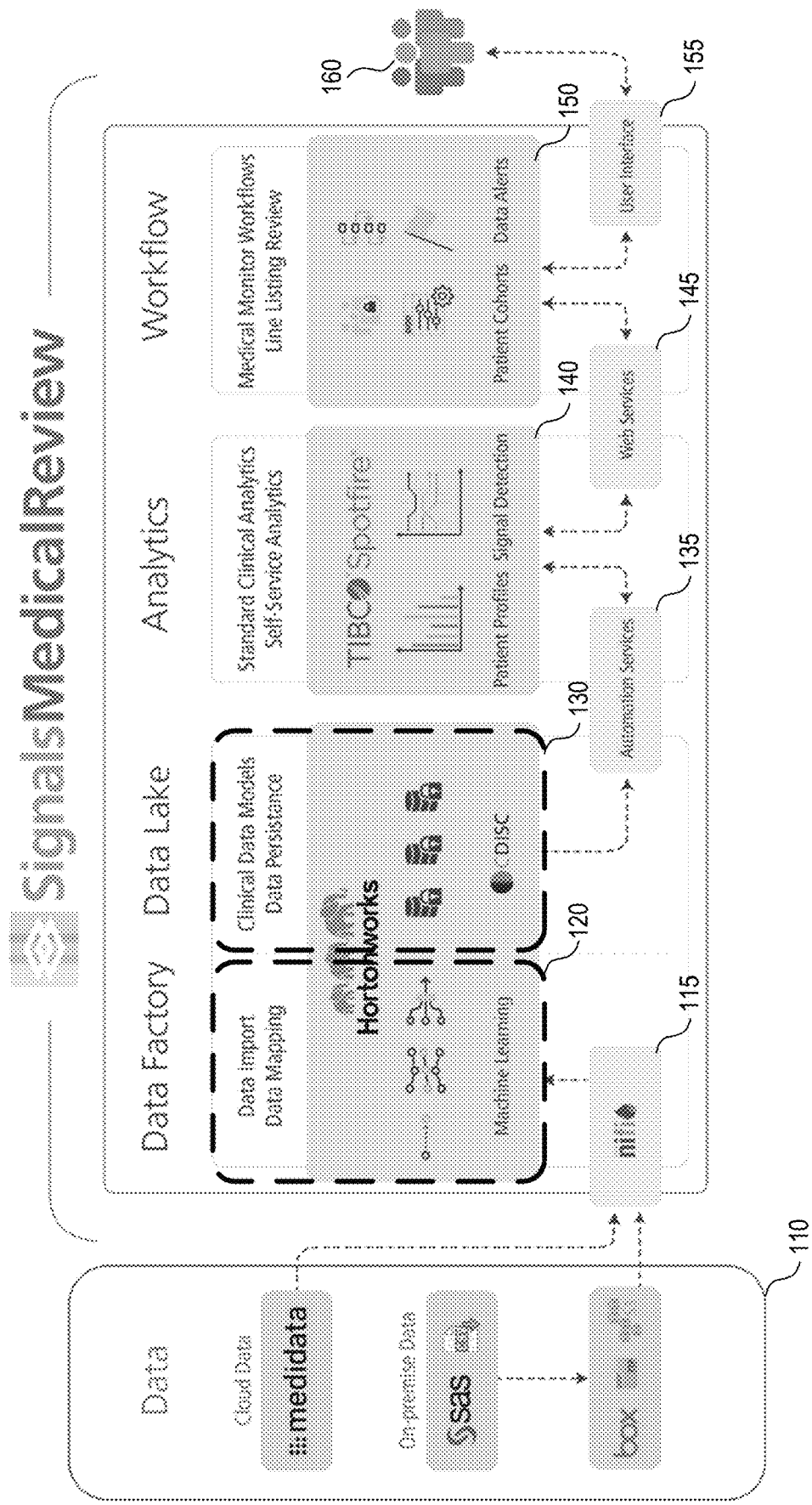
FIG. 1 is a schematic of an illustrative embodiment of a clinical data analysis system, in which one or more aspects may be implemented.

FIG. 1 illustrates an example clinical data analysis system 100 in which one or more aspects may find use. A user may seek to consolidate source clinical trial data from a variety of sources and stored according to a variety of schemas for use by an analytics platform, such as Perkin Elmer's Signals Medical Review. The analytics platform may operate on data stored in a "data lake," and may expect that data to be in a specific, target data schema. For example, the analytics platform may operate on data stored according to clinical data schemas approved and administered by the Food and Drug Administration (FDA). Aspects described herein may allow a user to designate a source data set and a target data platform, and may automatically handle mapping and transformation of the source data set to a target data set suitable for use on the target data platform. The user may be unaware of the data schema requirements of the platform, and automatic mapping and transformation may be transparent to the user other than confirmation and review. Some data platforms may support multiple schemas, and the computer may automatically select the most appropriate schema based on the source data.

The clinical data analysis system 100 may receive raw source clinical data 110 from various data sources. The raw source clinical data set 110 may be any source data in any format. In some instances the raw source clinical data 110 can be stored locally, while in other instances the data 110 can be stored in an offsite location such as cloud storage or another offsite data storage location. The raw source clinical data 110 can be provided to the clinical data analysis system 100 in a delimited file format such as a CSV or a tab delimited file format, while in other instances the raw source clinical data 20 can be provided in a SAS file, for example. The various data sources may be aggregated through an aggregating service 115, such as Nifi™. The aggregated data may be provided to a data import and data mapping module 120. Aspects described herein may be used to implement data import and data mapping module 120, improving the overall functionality of clinical data analysis system 100. The data content from the various data sources may come into the data import and data mapping module 120 in a variety of formats, but leaves as a unified set of data in a common schema.

The data mapping and transformation module 120 may be an artificial intelligence engine that leverages one or more deep learning algorithms to substantially automatically map the raw source clinical data 110 to a standard data schema, and then perform substantially automatic data transformations on the mapped raw source clinical data 110 to correct data discrepancies. This may help address any data quality issues inherent in the raw data. The algorithms within the data mapping and transformation module 120 may be learning algorithms that use mapped and transformed raw clinical data and the metadata associated therewith to update prediction models that are used by the learning algorithms to map and transform raw source clinical data 110. Although the processes carried out within the data mapping and transformation module 120 are automated, end users may also manually map raw source clinical data 110 to standard schemas within the clinical data analysis system 100. In one example, approximately eighty percent of all raw source clinical data 110 may be mapped using the learning algorithms and processes of the data mapping and transformation module 120, while the remaining twenty percent of the raw source clinical data 110 is manually mapped by an end user of the system 100. When raw source clinical data 110 is manually mapped, the resulting mapped data and the metadata associated therewith may be used by the data mapping and transformation module 120 to update the various prediction models to permit the algorithms of the data mapping and transformation module 120 to learn from an end user's manual mapping decisions.

Data processed by data import and data mapping module 120 (also called a "data factory") may be provided to a clinical data model and data persistence module 130 (comprising, and sometimes called, a "data lake"). The mapped and transformed clinical data may then be analyzed and used within workflows. Data from the data lake may be utilized by automation services 135, which may package the data for use by analytics programs 140. Web services 145 may allow analytics programs 140 to interface with medical monitoring systems 150, for example to generate data alerts for users and patients. User interfaces 155 may allow users 160 to interact which the clinical data analysis system 100, and facilitate decisions based on the clinical data.

Figure 2:
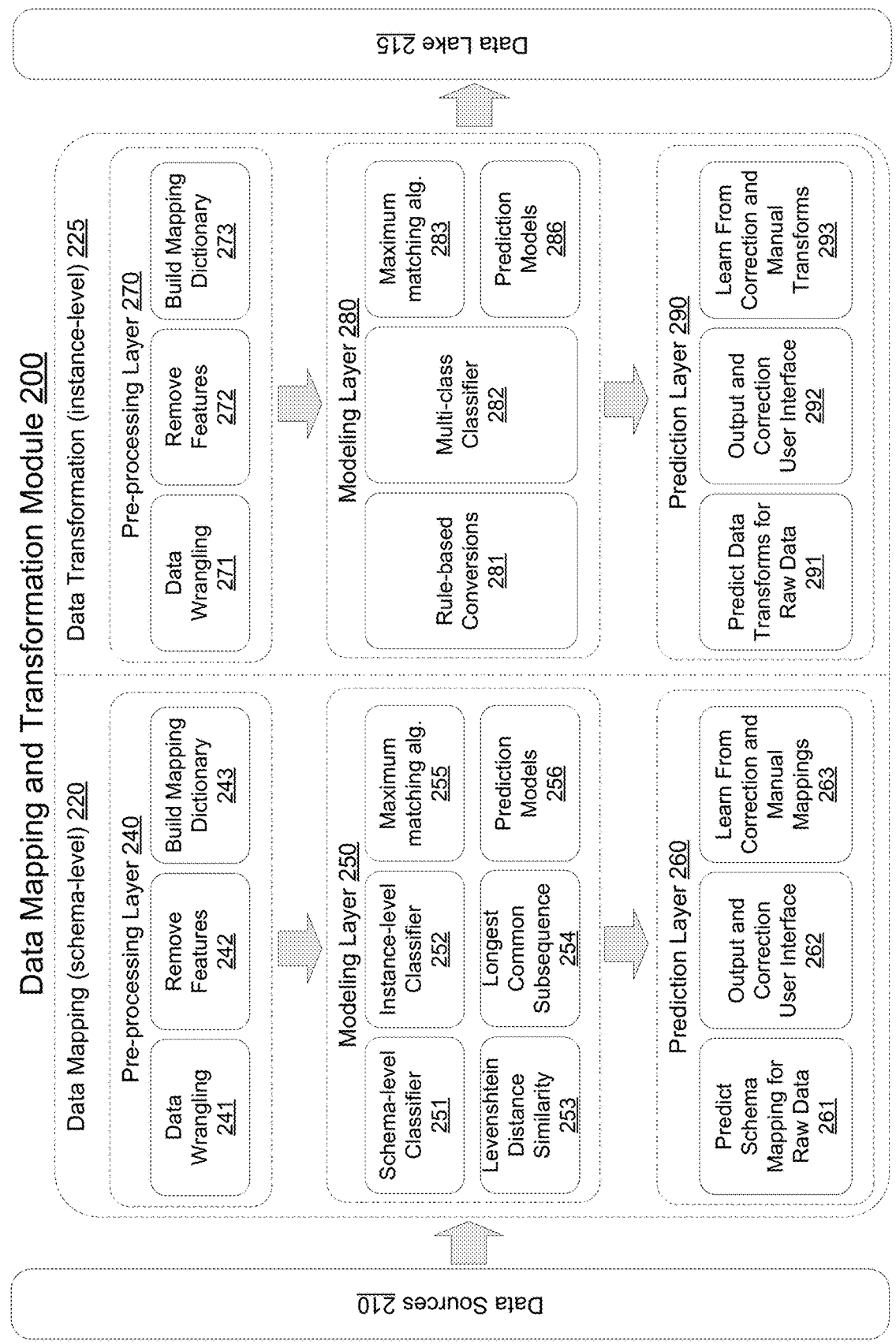
FIG. 2 is a block diagram of an illustrative embodiment of a data mapping and transformation module, according to one or more aspects.

FIG. 2 illustrates an illustrative data mapping and transformation module 200, according to aspects described herein. Data mapping and transformation module 200 may serve the role of data import and data mapping module 120 in FIG. 1. Data mapping and transformation module 200 may include submodules, such as a data mapping submodule 220 and a data transformation submodule 225. Together, data mapping submodule 220 and data transformation submodule 225 may comprise a two-step approach to schema mapping and data transformation.

A user may select one or more data source 210 as a source of raw clinical source data. Source data from data source 210 may be provided first to data mapping submodule 220 where the raw data, often in disparate data formats, can be mapped to a standard target data schema using a multi-step process that relies on various methods of classification, and then uses probability matrices to predict which schema mapping is best suited to map the raw clinical source data to the desired target data schema. Upon mapping the raw clinical source data to a standard target data schema, the data transformation submodule 220 may take the mapped raw clinical data and transform the raw data according to the selected standard target data schema, generating a target data set suitable for use by platform analytics tools.

Data processing submodule 220 may comprise a pre-processing layer 240, a modeling layer 250, and a prediction layer 260. Each of these layers form part of a larger process for mapping raw clinical data to a standard schema, and each of the layers can contain one or more classifiers, routines, and/or other submodules used by the data mapping submodule to generate a predicted target mapping that maps the fields of the source data schema to fields of the target data schema.

Pre-processing layer 240 may perform pre-processing on the source data set to render it more suitable for the techniques employed by data mapping submodule 220, or otherwise prepare the system to generate a predicted target schema mapping. Data wrangling component 241 may include the algorithms and processes required to obtain raw source clinical data. For example, data wrangling component 241 may implement one or more aspects of the pluggable connectors described in U.S. application Ser. No. 15/247,825, titled "Clinical Connector and Analytical Framework" and filed Aug. 25, 2016, incorporated by reference above. Remove useless features component 242 may pre-process the data to remove unneeded content, such as leading/trailing whitespace, formatting, and/or source columns with no target schema counterpart.

Build mapping dictionary component 243 may provide for training the artificial neural networks used as part of schema-level classifier 251 and instance-level classifier 252, discussed further below. The artificial neural networks may use a mapping dictionary comprising a training set of example inputs and outputs to determine weightings for use in the neural network predictive models. As discussed further herein, incorrect classifications/predicted mappings may be corrected by the user and fed back into the training process for the artificial neural network. A user-defined rule and/or mapping may be added to the training set so that the artificial neural network may learn from the user's example. The mapping dictionary may include a plurality of schema-to-schema mappings and/or field-to-field mappings. The schema-to-schema mappings may include, in an example implementation, a map of source column names and target column names. The mapping dictionary may be a dictionary of all possible schemas known to the system and may include known mappings between those schemas. The training set of data may be the whole known schema dictionary. As discussed further herein, the schema-level classifier may operate on field names while the instance-level classifier operates on data content. The mapping dictionary (as a training set) may include indications of field correspondence but also examples of data content and a corresponding target data field. The training set may comprise feature vectors related to the fields and/or data content of the source data and/or target data schema. For example, feature vectors may be useful to assist in developing a similarity measurement in Levenshtein distance similarity component 253 and/or longest common subsequence component 254. A feature vector may be used to track letter sequences from a-z (e.g., how many a's, b's, etc.) and two letter sequences (e.g., "ac" "ct").

Modeling layer 250 may receive the pre-processed source data from pre-processing layer 240 and begin the process of mapping the source data to a standard target schema based on the target data platform. Within the modeling layer 250 are various classification components including schema-level classifier 251, instance-level classifier 252, Levenshtein distance similarity classifier 253, and longest common subsequence similarity classifier 254.

Schema-level classifier 251 may include an artificial neural network trained based on source and target schema field names. Schema-level classifier 251 may use schema names as the matching factor. If schema-level classifier 251 detects a match just by looking at names of columns, it may be a strong signal regarding the proper mapping of the source data to the target data. The schema-level classifier 251 may be trained using a mapping dictionary, described above, that contains training examples of source and corresponding target field names. The schema-level classifier 251 may predict the schema for a set of raw data based on column names within that set of raw data; for example, if the columns within a set of data were live birth rate, then this descriptor would be used to predict the standard schema for the data in that column.

Instance-level classifier 252 may include another artificial neural network trained based on source content and target schema content. The instance-level classifier 252 neural network may be trained based on data content indications in the mapping dictionary. The instance-level classifier 252 may predict the schema for a set of raw source data based on the content of the data. The instance-level classifier 252 may assess the content of the source data records and the content of example target schema data, and generate a prediction based on that. Example types of methods to look at matching at the instance level may include a data type of the columns, a number of whitespaces in a column, an average amount of included whitespace, and the like. For example, if the data included hemoglobin amounts, then this content characterization would be used to predict the target field corresponding to the data in that column, which may inform selection of the target data schema and mapping.

The Levenshtein distance similarity classifier 253 may assess the similarity between the column names of a set of raw source clinical data and the column names of a possible standard target schema. Levenshtein distance may represent a similarity between source and target column names. Lower values may represent better, "closer" matches. Levenshtein distance similarity classifier 253 may determine a value representative of the similarity between the actual column name and a proposed column name. Using this value, the Levenshtein distance similarity classifier may predict a standard target schema for the data based on the Levenshtein distance between the fields.

Similarly, the longest common subsequence similarity classifier 254 may assess the similarity between the column names of a source data set and the column names of a proposed target schema based on a longest common subsequence (LCS) matching criteria. The LCS criteria may seek to identify a longest shared (common) subsequence of characters between a source field name and a set of candidate target field names. This may be accomplished using feature vectors comprised of various character subsequences within the field names. For example, the source field "Action" may map to "Final Action" instead of "Activity" based on the LCS criteria.

In some embodiments, the models and data required to carry out the classification algorithms of the modeling layer 250 are stored in a prediction models storage area 256 of that layer. The classification algorithms may be used to make at least four predictions of a possible standard target schema for a particular set of raw source clinical data. According to some embodiments, the four predictions may be based on the output of (1) a schema-level classifier 251, (2) an instance-level classifier 252, (3) a Levenshtein distance similarity classifier 253, and (4) a longest common subsequence classifier 254. Some embodiments may incorporate one or both similarity matching classifiers. Predictions generated by the various classifiers and components may have associated with them a value representative of the probability that the proposed target schema and/or field is the correct standard schema/field to apply given the name and/or content of the source field. Modeling layer 250 may include a maximum matching algorithm component 255 to determine a maximum match for a proposed/predicted mapping for a source field to a target field based on a weighted combination of the predictions from the classifiers.

Modeling layer 250 may represent the deep learning classifiers and algorithms used to determine a mapping from the source data schema to the target data schema. If the modeling layer represents the artificial neural networks and classifiers themselves, prediction layer 260 may represent the use of, output from, and feedback to that artificial neural network layer. The modeling layer 250 may build the model, and prediction layer 260 may output the predictions of the model for review by the user and further use by the data transformation submodule 225.

Prediction layer 260 may comprise several components and/or functions. Prediction layer 260 may operate to predict schema mappings for raw source data via component 261. Prediction component 261 may employ maximum matching algorithm component 255 to generate a weighted combination of the predictions generated by each of the classifiers in the modeling layer 250. The weighted combination may be used to determine a final prediction of the models, which may be output to the user for correction via user interface 262. The final predicted schema mapping may be presented to the user, and the user may be allowed to change the mapping for one or more fields of the source data schema or the target data schema. Any user corrections may be fed back to the modeling layer 250 components and mapping dictionary 243 via learning component 263, which allows the classifiers to learn from user corrections and the input of manual mappings.

This feedback loop may be particularly effective in training the system to recognize situations it was not previously able to handle. For example, at the outset the artificial neural networks might make a best guess based on a limited training set and fail to accurately predict a proper mapping between the source data set and a target data schema. As users correct predicted mappings and/or enter manual mappings, the mapping dictionary training set may grow and the predictive accuracy of the artificial neural networks may increase.

Data transformation submodule 225 may operate at an instance-level (e.g., content level) to transform the source data set to a target data set conforming to the target data schema. Like the data mapping submodule 220, the data transformation submodule 225 may have a preprocessing layer 270, a modeling layer 280 and a prediction and user feedback layer 290. Each of these layers form part of a larger process for transforming raw source clinical data according to a standard target schema, and each of the layers may contain one or more algorithms. Preprocessing layer 270 may include algorithms and processes for taking the raw source clinical data and passing it through to the modeling layer 280 where a determination may be made as to how the data should be transformed. Like data mapping submodule 220's pre-processing layer 240, the pre-processing layer 270 of data transformation submodule 225 may comprise a data wrangling component 271, a remove useless features component 272, and a build mapping dictionary component 273. Each of these performs similar features to its counterpart in the data mapping submodule 220.

Modeling layer 280 may comprise several classifiers that operate in concert to generate predictions regarding suitable data transformations to take content of a source field and generate suitable content for a corresponding target field. Once it is identified that a particular source field corresponds to a particular target field, rule-based conversions classifier 281 and multi-class classifier 282 may be employed to determine how to transform source data content of the source field to match an expected data format associated with the mapped corresponding target field. Rule-based conversions classifier 281 may be trained and/or otherwise configured to assess the format and nature of the source field data content to determine whether a rule-based conversion exists for that data content. The rule-based conversions may also consider the mapped target field corresponding to the source field. For example, if that nature and character of the source field data content is a date/time entry, the rules-based conversion may specify how a date in a first format is converted to a date in a second format. In an example, a source data set may comprise dates in a MM-DD-YY format while a target data set may require dates in a YYYY-MM-DD format. Other example data formats that may be subject to rule-based conversions include Boolean fields, which may have their values represented as true/false, yes/no, and 0/1 (for example).

Not all data transformations will be handled through rule-based conversions, however. More complex fields, such as categories, may require further processing to predict and select a suitable data transformation to get the source data into a proper format. Multi-class classifier 282 may comprise an artificial neural network trained based on examples in a mapping dictionary that indicates how data from source fields should be transformed to arrive at suitable formats for a mapped corresponding target field. A similar process to that used in determining mappings may be used to determine suitable transformations to go from complex formats in source data to corresponding formats in target data. Multi-class classifier 282 may apply a mapping dictionary to tie source/target categories together and generate predicted probability levels for each suggested transformation. Other classifiers may be used as appropriate. A maximum matching algorithm component 283 may specify weights for use in generating a weighted combination of the predicted transformations and determine a maximum match across the classifiers. Models used by the modeling layer 280 may be stored in prediction model area 286.

The models of modeling layer 280 may be used by prediction layer 290 to predict data transformations for the raw source data in component 291. Output of the classifiers may be used to generate a weighted combination of the predictions and maximum matching algorithm component 283 may be used to determine a final prediction for the data transformation. The predicted data transformation may be output to a user for review and correction via user interface 292. User corrections and manually entered transformations may be fed back to modeling layer 280 and mapping dictionary 273, allowing the classifiers of data transformation submodule 225 to further learn and become better able to assist users in automatically determining suitable data transformations.

The mapping determined by data mapping submodule 220 and the data transformations determined by data transformation submodule 225 may be used to transform raw source data from data sources 210 to generate a suitable target data set that complies with a desired target schema. The generated target data set may be stored in data lake 215 for use by analytics tools.

Figure 3:
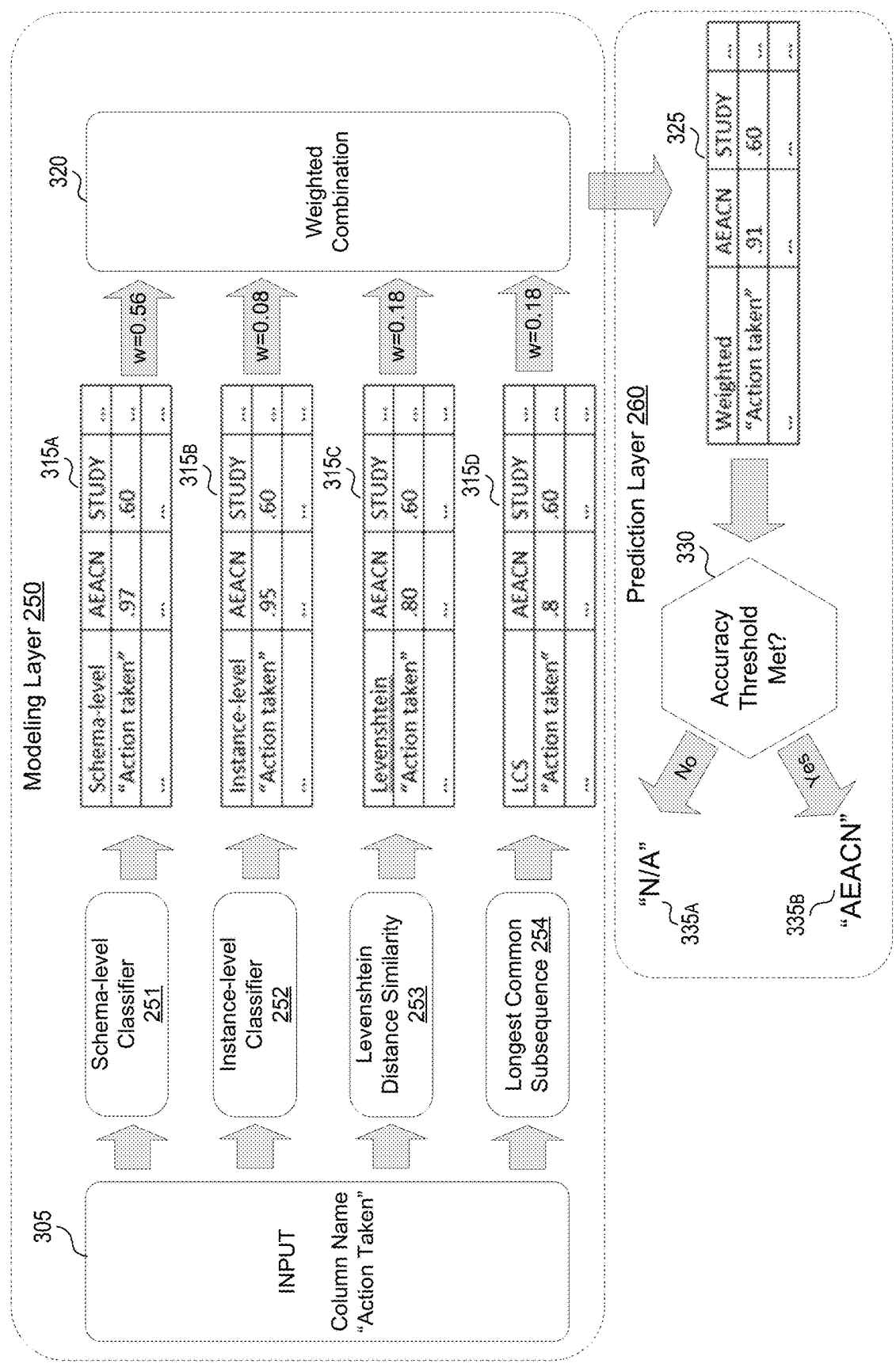
FIG. 3 is a block diagram of an illustrative example of a schema mapping method according to one or more aspects.

FIG. 3 illustrates operation of data mapping submodule 220, according to some aspects, which may generate a mapping of fields in a source data set to fields in a target data schema. Input 305 may comprise source data, which may have been subject to pre-processing by pre-processing layer 240. For example, the source data of input 305 may comprise data content in a column named "Action Taken." Input data 305 may be passed into four classifiers: schema-level classifier 251, instance-level classifier 252, Levenshtein distance similarity classifier 253, and longest common subsequence classifier 254. As discussed above, these classification algorithms are (respectively): 1) a schema-level classification algorithm that may use artificial neural networks to predict the correct column mapping based on the raw data column names; 2) an instance-level classification algorithm that may try to predict the correct column mapping based on the raw data column content; 3) a Levenshtein distance similarity algorithm that calculates the distance between raw data column names and target column names; and 4) a longest common subsequence similarity algorithm that calculates the distance between raw data column names and target column names.

The four classification algorithms may be applied to generate multiple probability matrices 315A-D, each indicating the likelihood that the source field "Action Taken" corresponds to each respective target field, such as "AEACN" and "STUDY." The fields/columns of the source data set may be run through the series of four classification algorithms to generate the prediction and probability results which are used to build probability matrices 315A-D. The probability matrices may contain mapping predictions made by each classification algorithm and the probability that the predicted mapping is the correct mapping. For example, the schema-level classification algorithm can predict a mapping to "AEACN" with a 97% probability of being correct, while the Levenshtein distance classification algorithm can predict a mapping to "AEACN" with a 80% probability of being correct.

At component 320, the four probability matrices may be used to generate a weighted probability matrix 325. Weightings for each classifier algorithm may be tuned based on particular applications an experience. For example, as illustrated in FIG. 3, the schema-level classifier 251 may have a weight of 0.56, the instance-level classifier 252 may have a weight of 0.08, the Levenshtein classifier 253 may have a weight of 0.18, and the LCS classifier 254 may have a weight of 0.18. The schema-level classifier 251 offers particularly strong predictive value, and thus may be assigned a high weighting. In practice, a weighting of 0.50 (50%) or more for the schema-level classifier 251 may be beneficial. In the example, if each of the four classification algorithms predicted that the raw column data should be mapped to the "AEACN" schema with the following probabilities: 97%, 95%, 80% and 80%; then the weighted probability matrix 325 would include a schema prediction of "AEACN" with a probability of 91% (i.e., combining the predictions with their associated weights). Based on the weighted probability matrix 325, a maximum matching algorithm may be employed by prediction layer 260 to determine the best match predicted mapping between the source field and one or more target fields. The best match may be compared against an accuracy threshold at step 330. For example, the system may only produce a predicted mapping for the source field if it has 90% confidence in the prediction. If the accuracy threshold is met, the system may output the prediction value, e.g., "AEACN" at step 335B. If the accuracy threshold is not met, the system may decline to output a prediction, and may output a default or non-value such as "N/A" at step 335A. chooses the best schema mapping.

Again, data transformation predictions by data transformation submodule 225 proceed according to a similar process. Data transformation, in some instances, only happens on columns of raw source data that have been mapped to a target schema. The process used to transform raw source data may be similar to the process used to map a schema to the raw data in that a comparison may be made between the unique instances coming from the raw data sets and the instances expected in the target dataset. After making the comparison, a prediction may be made as to which transform should be applied to the raw source data to generate properly formatted target data content.

Figure 4:
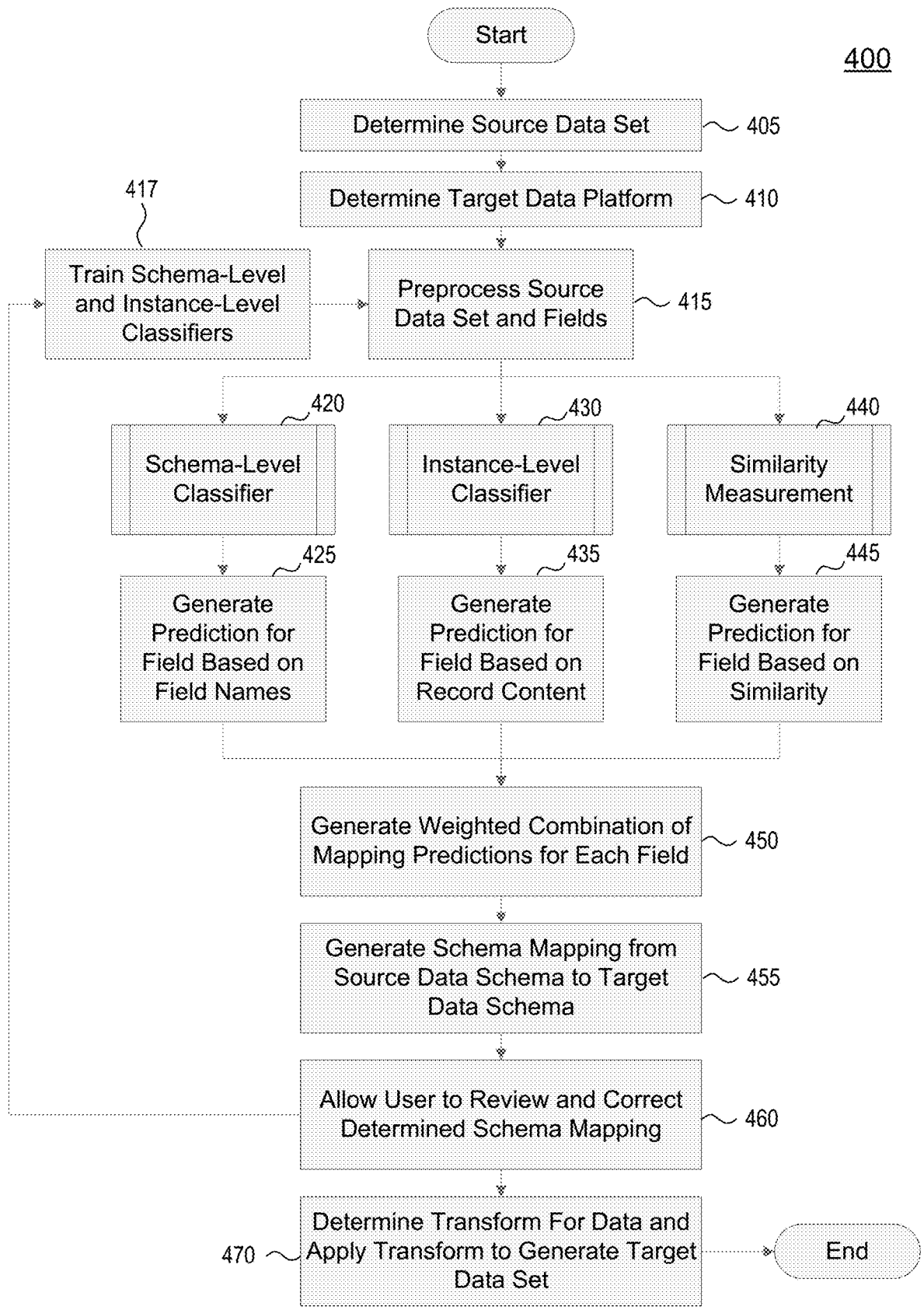
FIG. 4 is a flowchart illustrating an example method of generating a schema mapping, according to one or more aspects.

FIG. 4 illustrates a method 400 for automating source data mapping and transformation to a target data schema. Method 400 may be performed by any suitable computing device and/or system configured to perform the specific steps described herein. Method 400 may also be embodied in computer-readable media storing instructions causing a computing device and/or system to perform those steps. And, similarly, method 400 may be embodied in a suitably configured computing device and/or system.

At step 405, the system may determine a source data set. The source data set may be identified by a user. The user may identify a set of raw data, such as clinical data, that the user wishes to have mapped and transformed to a format suitable for use on a target data platform. At step 410, the user may identify the target data platform and/or target data schema for the mapping and transformation. The order of indications does not matter, and in some embodiments the user may provide a single indication of the source data and target platform. In some embodiments, the indication of target data platform may be implied. For example, if the user is selecting data through a particular analytics platform, it may be assumed that the user wishes for data in a format suitable for use on the analytics platform.

At step 415, the system may pre-process the source data set and/or fields. For example, the system may parse source data content to render the content more suitable for review by the classifier algorithms. Cleaning up the data may comprise removing leading or trailing whitespace, removing formatting of the content, and the like. The system may also remove useless features from the source data set. For example, the system may remove source data columns that are not relevant to the target data platform.

At step 417, the system may train schema-level and instance-level classifiers. Each classifier may comprise a respective artificial neural network trained on an example data set of mappings from known source fields to respective known target fields. These mappings may be schema-to-schema and/or field-to-field. The training set may be initialized with common and known mappings, and may be updated during operation of the system as users provide corrected and manual mappings.

After pre-processing, the system may process the source data set to generate predicted mappings using at least three classifiers: a schema-level classifier, an instance-level classifier, and one or more classifiers based on a similarity measurement.

At step 420, the system may process the source data fields using a schema-level classifier trained to generate predictions based on source field names and target field names in step 425. At step 430, the system may process the source data content using an instance-level classifier trained to generate predictions based on source field data content and target field data content in step 435. And at step 440, the system may process the source data fields and the target data fields using at least one similarity measurement classifier to generate predictions based on applying a similarity criteria to a source field name and a target field name. Example similarity criteria include Levenshtein distance and longest common subsequence (LCS). Example embodiments may employ both Levenshtein distance and LCS to generate more robust predictions.

At step 450, the system may generate a weighted combination of the mapping predictions for each field. The weighted combination may be generated based on applying a corresponding weighting value to the results from each classifier. Each classifier may generate a list of probabilities that a given source field corresponds to each respective target field. The probabilities given by each classifier may be combined according to the assigned weight, and a weighted probability may be obtained for each source field/target field combination.

At step 455, the system may generate a schema mapping from the source data schema to the target data schema. The schema mapping may be based on the field mappings determined for each source field.

At step 460, the system may present the user with the determined predicted schema mapping. The user may be allowed to view the correspondence between source fields and target fields, and the user may make corrections and/or assign manual mappings. A user interface may be employed to facilitate user interaction with the predicted schema. For example, a user interface such as that provided in U.S. application Ser. No. 15/247,821, titled "Systems and Method Employing Merge Technology for the Clinical Domain" and filed Aug. 25, 2016, incorporated above by reference, may be used to display the mapping to the user. The user may, for example, drag and drop fields relative to one another to visually define the mapping from the source data schema to the target data schema. Any user corrections and/or manual mappings may be fed back into the training set used to train the schema-level and instance-level classifiers in step 417.

At step 470, the system may determine a data transform based on the source data schema, the target data schema, and the determined mapping. The determined data transform may be applied to the source data set to generate a target data set. The generated target data set, now in a format suitable for use by analytics software on the target data platform, may be stored in a data lake and made accessible to the analytics software. After step 470, the method may end.

Figure 5:
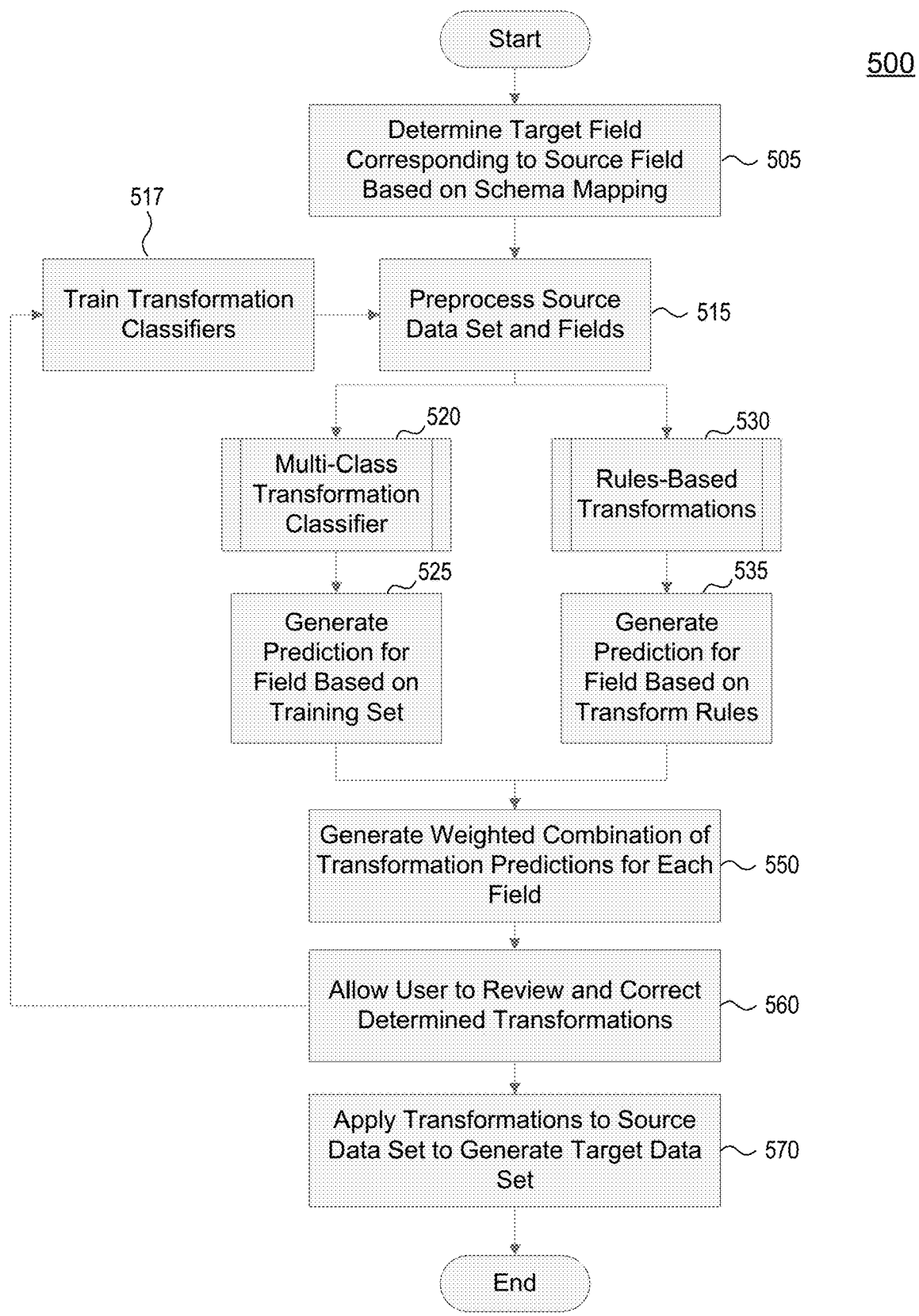
FIG. 5 is a flowchart illustrating an example method of generating a set of data transformations, according to one or more aspects.

FIG. 5 provides further details relevant to how the system may determine the data transform. Method 500 may determine a suitable set of transformations to apply to the source data to arrive at a properly formatted result. As with method 400, method 500 may be implemented by any suitable computing device and/or system, embodied in computer-readable media, and/or embodied in a suitably configured computing device and/or system.

At step 505, the system may determine a target field corresponding to a particular source field based on the schema mapping determined in step 455 of method 400.

At step 515, the system may pre-process the source data field and/or content to remove useless and/or unnecessary features, as described above, to render the data more suitable for use by the classifiers.

At step 517, the system may train one or more artificial neural networks associated with the transformation classifiers. For example, the system may train a multi-class artificial neural network classifier based on a training set of examples matching complex-type source fields to corresponding target fields.

After pre-processing, the system may generate predicted transformations for each field using a multi-class transformation classifier and a rules-based transformation classifier. At step 520, the system may process the source field and content using a multi-class transformation classifier to generate a prediction for the field based on the training set of complex-type source fields to corresponding target fields at step 525. Other artificial neural networks and training sets may also be used to generate predictions for the suitable data transformations. At step 530, the system may process the source field and content using a rules-based transformation classifier to generate a prediction for the field based on transformation rules at step 535.

At step 550, the system may generate a weighted combination of the transformation predictions for each field. The system may generate a final predicted transformation for each source field that is suitable to generate the target data set having content corresponding to that of the source data set but formatted according to the target schema.

At step 560, the predicted transformations may be presented to the user for review and correction. The user may enter corrections to the transformations and/or provide manually entered transformations via a user interface. Any user corrections and/or manual entries may be fed back to the training set in step 517.

At step 570, the system may apply the transformations to the source data set to generate the target data set. The target data set, which includes content corresponding to the source data set but formatted according to the target schema, may be stored in a data lake for use by applications on the target data platform.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer implemented method for data mapping and transformation, the method comprising:
   determining a source data set, wherein the source data set comprises a plurality of source data records organized according to a source data schema comprising a plurality of source fields;
   determining a target data platform, wherein the target data platform is associated with a target data schema comprising a plurality of target fields;
   generating, by a computing device, a schema-level prediction for a target mapping of a first source field, of the plurality of source fields, based on output of a schema-level classifier, wherein the schema-level classifier comprises a first artificial neural network trained based on first example mappings between source field names and target field names;
   generating, by the computing device, an instance-level prediction for the target mapping of the first source field based on output of an instance-level classifier, wherein the instance-level classifier comprises a second artificial neural network trained based on second example mappings between source field data record characteristics and target field data record characteristics;
   generating, by the computing device, one or more similarity predictions for the target mapping of the first source field based on one or more similarity measurements;
   generating, by the computing device, a schema mapping of the source data schema to the target data schema based on a weighted combination of the schema-level prediction, the instance-level prediction, and the one or more similarity predictions for the target mapping of the first source field;
   transforming, by the computing device, the plurality of source data records based on the schema mapping of the source data schema to the target data schema; and
   storing the transformed source data records as a target data set.

2. The method of claim 1, wherein the schema-level prediction, the instance-level prediction, and the one or more similarity predictions for the target mapping of the first source field each comprise a list of probabilities that the first source field corresponds to each respective target field of the plurality of target fields.

3. The method of claim 1, further comprising:
   causing display of the schema mapping to a user via a user interface;
   receiving user input comprising at least one modification to the schema mapping; and
   updating the schema mapping based on the at least one modification.

4. The method of claim 3, further comprising:
   updating the first example mappings based on the updated schema mapping, wherein the first artificial neural network is further trained based on the updated first example mappings; or
   updating the second example mappings based on the updated schema mapping, wherein the second artificial neural network is further trained based on the updated second example mappings.

5. The method of claim 1, wherein transforming the plurality of source data records based on the mapping of the source data schema to the target data schema comprises:

generating, by the computing device and based on a first target field associated with the first source field in the schema mapping, a first data transformation for portions of each source data record corresponding to the first source field; and applying the first data transformation to the portions of each source data record corresponding to the first source field.

6. The method of claim 5, wherein generating the first data transformation for portions of each source data record corresponding to the first source field comprises:

generating one or more predictions for the first data transformation based on output of a data classifier, wherein the data classifier comprises a third artificial neural network trained based on example transformations for data corresponding to the first source field and the associated first target field.

7. The method of claim 6, further comprising:

causing display of the first data transformation to a user via a user interface;

receiving user input comprising at least one modification to the first data transformation; and updating the first data transformation based on the at least one modification.

8. The method of claim 7, further comprising:

updating the example transformations based on the updated first data transformation, wherein the third artificial neural network is further trained based on the updated example transformations.

9. The method of claim 5, wherein generating the first data transformation comprises:

selecting, based on the first source field or the associated first target field, a rule-based conversion data transformation as the first data transformation.

10. The method of claim 1, further comprising:

pre-processing the source data set to remove at least one source field.

11. The method of claim 1, further comprising:

pre-processing the source data set to modify one or more source data records, of the plurality of source data records, to remove whitespace or formatting.

12. The method of claim 1, wherein generating the one or more similarity predictions for the target mapping of the first source field based on one or more similarity measurements comprises:

generating a first similarity prediction for the target mapping of the first source field based on a Levenshtein distance similarity criteria.

13. The method of claim 1, wherein generating the one or more similarity predictions for the target mapping of the first source field based on one or more similarity measurements comprises:

generating a second similarity prediction for the target mapping of the first source field based on a longest common subsequence similarity criteria.

14. The method of claim 1, wherein generating the one or more similarity predictions for the target mapping of the first source field based on one or more similarity measurements comprises:

generating a first similarity prediction for the target mapping of the first source field based on a Levenshtein distance similarity criteria; and generating a second similarity prediction for the target mapping of the first source field based on a longest common subsequence similarity criteria.

15. The method of claim 1, wherein the schema-level prediction is assigned at least 50% of the weight in the weighted combination of the schema-level prediction, the instance-level prediction, and the one or more similarity predictions for the target mapping of the first source field.

16. The method of claim 1, wherein the plurality of source fields correspond to columns in the source data set.

17. The method of claim 1, wherein the characteristics of the source field data record comprise a data type of the source field data record.

18. The method of claim 1, wherein the characteristics of the source field data record comprise a number of whitespaces in the in the source field data record.

19. The method of claim 1, wherein the characteristics of the source field data record comprise an average amount of included whitespace in the source field data records.

20. A system comprising:

a source data storage device storing a source data set, wherein the source data set comprises a plurality of source data records organized according to a source data schema comprising a plurality of source fields;

a target data storage device, wherein the target data storage device is associated with a target data schema comprising a plurality of target fields;

one or more processors; and memory storing instructions that, when executed by the one or more processors, cause the one or more processors to:

generate a schema-level prediction for a target mapping of a first source field, of the plurality of source fields, based on output of a schema-level classifier, wherein the schema-level classifier comprises a first artificial neural network trained based on first example mappings between source field names and target field names;

generate an instance-level prediction for the target mapping of the first source field based on output of an instance-level classifier, wherein the instance-level classifier comprises a second artificial neural network trained based on second example mappings between source field data record characteristics and target field data record characteristics;

generate one or more similarity predictions for the target mapping of the first source field based on one or more similarity measurements;

generate a schema mapping of the source data schema to the target data schema based on a weighted combination of the schema-level prediction, the instance-level prediction, and the one or more similarity predictions for the target mapping of the first source field;

generate, for each respective target field associated with a respective source field in the schema mapping, a respective data transformation for portions of each source data record corresponding to the respective source field;

apply the data transformations for each respective target field to the portions of each source data record corresponding to the respective source fields; and cause storage of the transformed source data records as a target data set by the target data storage device.

21. The system of claim 20, wherein the memory further stores instructions that, when executed by the one or more processors, cause the one or more processors to generate the respective data transformations for each respective target field by causing the one or more processors to:

generate one or more predictions for the respective data transformation based on output of a data classifier, wherein the data classifier comprises a third artificial neural network trained based on example transformations for data corresponding to the respective source field and the associated respective target field.

22. One or more non-transitory computer readable media storing instructions that, when executed by one or more processors, cause the one or more processors to perform steps comprising:

determining a source data set, wherein the source data set comprises a plurality of source data records organized according to a source data schema comprising a plurality of source fields;

determining a target data platform, wherein the target data platform is associated with a target data schema comprising a plurality of target fields;

generating, by a computing device, a schema-level prediction for a target mapping of a first source field, of the plurality of source fields, based on output of a schema-level classifier, wherein the schema-level classifier comprises a first artificial neural network trained based on first example mappings between source field names and target field names, and wherein the schema-level prediction comprises a first list of probabilities that the first source field corresponds to each respective target field of the plurality of target fields;

generating, by the computing device, an instance-level prediction for the target mapping of the first source field based on output of an instance-level classifier, wherein the instance-level classifier comprises a second artificial neural network trained based on second example mappings between source field data record characteristics and target field data record characteristics, and wherein the instance-level prediction comprises a second list of probabilities that the first source field corresponds to each respective target field of the plurality of target fields;

generating, by the computing device, one or more similarity predictions for the target mapping of the first source field based on one or more similarity measurements, wherein the one or more similarity predictions each comprise a respective third list of probabilities that the first source field corresponds to each respective target field of the plurality of target fields;

generating, by the computing device, a schema mapping of the source data schema to the target data schema based on a weighted combination of the schema-level prediction, the instance-level prediction, and the one or more similarity predictions for the target mapping of the first source field;

causing display of the schema mapping of the source data schema to the target data schema to a user via a user interface;

receiving user input comprising at least one modification to the schema mapping;

updating the schema mapping based on the at least one modification;

transforming, by the computing device, the plurality of source data records based on the updated schema mapping; and storing the transformed source data records as a target data set.

23. The computer readable media of claim 22, wherein the instructions, when executed by the one or more processors, further cause the one or more processors to:

update the first example mappings based on the updated schema mapping, wherein the first artificial neural network is further trained based on the updated first example mappings.

* * * * *